US006284774B1

(12) United States Patent
Wright et al.

(10) Patent No.: US 6,284,774 B1
(45) Date of Patent: Sep. 4, 2001

(54) 4-BENZYL PIPERIDINE ALKYLSULFOXIDE HETEROCYCLES AND THEIR USE AS SUBTYPE-SELECTIVE NMDA RECEPTOR ANTAGONISTS

(75) Inventors: Jonathan L. Wright; Suzanne Ross Kesten, both of Ann Arbor, MI (US); Ravindra B. Upasani, Foothill Ranch; Nancy C. Lan, South Pasadena, both of CA (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/674,298

(22) PCT Filed: Jun. 25, 1999

(86) PCT No.: PCT/US99/14291

§ 371 Date: Oct. 31, 2000

§ 102(e) Date: Oct. 31, 2000

(87) PCT Pub. No.: WO00/00197

PCT Pub. Date: Jan. 6, 2000

Related U.S. Application Data

(60) Provisional application No. 60/090,914, filed on Jun. 26, 1998.

(51) Int. Cl.$^7$ ................... C07D 401/02; A61K 31/445
(52) U.S. Cl. .............. 514/321; 514/322; 546/197; 546/198; 546/199
(58) Field of Search .................. 514/321, 323; 546/197, 198, 199

(56) References Cited

U.S. PATENT DOCUMENTS

| 4,353,913 | 10/1982 | Wollweber et al. | 548/306 |
|---|---|---|---|
| 5,192,751 | 3/1993 | Thor | 514/82 |
| 5,698,553 | 12/1997 | Prucher et al. | 514/222.8 |

FOREIGN PATENT DOCUMENTS

| 2270359 | 4/1999 | (CA) . |
| 488959A | 6/1992 | (EP) . |
| 97/23216 | 3/1997 | (WO) . |
| 98/18793 | 5/1998 | (WO) . |

OTHER PUBLICATIONS

M. Gossel et al., "Effects of Coadministration of Glutamate–Receptor Antagonists and Dopaminergic Agonists on Locomotion in Monoamine–Depleted Rats," J. Neural Transmission, Parkinsons Disease and Dimentia, vol. 10(1), pp. 27–39 (1995) (Abstract No. 04452217).

T. Klockgether & L. Turski, Ann. Neurol., vol. 34, pp. 585–593 (1993).
P.T. Francis et al., J. Neurochem., vol. 60 (5), pp. 1589–1604 (1993).
S. Lipton, TINS vol. 16 (12), pp. 527–532 (1993).
Tiseo et al., J. Pharmacol. Exp Ther., vol. 264, pp. 1090–1096 (1993).
Marek et al., Brain Res., vol. 547, pp. 77–81 (1991).
Lufty et al., Brain Res., vol. 616, pp. 83–88 (1993).
Herman et al., Neuropsychopharmacology, vol. 12, pp. 269–294 (1995).
S.A. Lipton & P.A. Rosenberg, New Eng. J. Med., vol. 330(9), pp. 613–622 (1994).
C.F. Bigge, Biochem. Pharmacol., vol. 45, pp. 1547–1561 (1993).
Basile et al., Nature Medicine, vol. 2, pp. 1338–1344 (1996).
Curtis et al., Nature, vol. 191, pp. 1010–1011 (1961).
Lauritzen et al., Brain Res., vol. 475, pp. 317–327 (1988).
Vera & Nadelhaft, Neuroscience Letters, vol. 134, pp. 135–138 (1991).
B.V. Clineschmidt et al., Drug Dev. Res., vol. 2, pp. 147–163 (1982).
E.W. Anthony, Eur. J. Pharmacol., vol. 250, pp. 317–324 (1993).
J. Winslow et al., Eur. J. Pharmacol., vol. 190, pp. 11–22 (1990).
R. Dunn et al., Eur. J. Pharmacol., vol. 214, pp. 207–214 (1992).
J.H. Kehne et al., Eur. J. Pharmacol., vol. 193, pp. 283–292 (1991).
P.H. Hutson et al., Br. J. Pharmacol., vol. 103, pp. 2037–2044 (1991).
L.J. Bristow et al., Br. J. Pharmacol., vol. 108, pp. 1156–1163 (1993).
Rojas et al., Drug Dev. Res., vol. 29, pp. 222–226 (1993).
Sonsalla et al., Science, vol. 243, pp. 398–400 (1989).
Carlsson et al., Trends Neurosci., vol. 13, pp. 272–276 (1990).
L.D. Snell et al., J. Pharmacol. Exp Ther., vol. 235, pp. 50–57 (1985).
W. Danysz et al., J. Neural Trans., vol. 7, pp. 155–166 (1994).
Trujillo et al., Science, vol. 251, pp. 85–87 (1991).
Said, S.J., Trends in Pharmacol. Sci., vol. 20, pp. 132–134) 1999.

*Primary Examiner*—Zinna Northington Davis
(74) *Attorney, Agent, or Firm*—Fitzpatrick, Cella, Harper & Scinto

(57) ABSTRACT

Novel 4-Benzyl piperidine alkylsulfoxide heterocycles are disclosed and their use as subtype selective NMDA receptor antagonists, particularly for the treatment of Parkinson's disease, most preferably in combination with L-DOPA.

28 Claims, No Drawings

4-BENZYL PIPERIDINE ALKYLSULFOXIDE HETEROCYCLES AND THEIR USE AS SUBTYPE-SELECTIVE NMDA RECEPTOR ANTAGONISTS

This application is a 371 application of PCT/US99/14291 filed Jun. 25, 1999 which claims priority to provisional application No. 60/090,914 filed Jun. 26, 1998.

BACKGROUND OF THE INVENTION

Field of the Invention

This invention is related to 4-benzyl piperidine alkylsulfoxide heterocycles. The compounds of this invention are selectively active as antagonists of N-methyl-D-aspartate (NMDA) receptor subtypes. The invention is also directed to the use of 4-benzyl piperidine alkyl sulfoxide heterocycles as neuroprotective agents for treating conditions such as stroke, cerebral ischemia, central nervous system trauma, macular and other retinal degenerative diseases, hypoglycemia, anxiety, psychosis, asthma, glaucoma, CMV retinitis, urinary incontinence, tinnitus, aminoglycoside antibiotics-induced hearing loss, convulsions, migraine headache, chronic pain, depression, opioid tolerance or withdrawal, or neuro-degenerative disorders such as lathyrism, Alzheimer's Disease, Parkinson's Disease and Huntington's Disease. A particularly preferred use of the compositions of this invention is in the treatment of Parkinson's Disease.

4-Benzyl piperidine analogs that are useful as subtype-selective NMDA receptor antagonists are described in PCT International Publication No. WO 97/23216. However, piperidine analogs having sulfoxide functionality are not described.

Benzylpiperidine derivatives are also disclosed in U.S. Pat. No. 5,698,553, as having the formula:

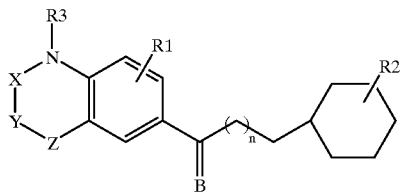

in which

R$^1$ is H, Hal or nitro,

R$^2$ is a benzyl group, which is unsubstituted or substituted by Hal on the aromatic portion, in the 2-, 3- or 4-position of the piperidine ring, with the proviso that R$^2$≠4-benzyl, i.e., R$^2$ is not in the 4-position of the piperidine ring, if X is —CO—, Y and Z are —CH$_2$— and R$^1$ is H, R$^3$ is H or A, X is —O—, —S—, —NH—, —CO— or —SO$_2$—, Y is —CH$_2$—, —O—, —S—, —NH— or alternatively —CO— if X is —CO— and Z is —NH— or —NA—, Z is —CH$_2$—, —C(A)$_2$—, —CH$_2$CH$_2$—, —CH=CH—, —CO—, —NH—, —NA—, —O—, —S— or a bond, wherein X-Y or Y-Z is not —O—O—, —S—S—, —NH—O—, —O—NH—, —NH—NH—, —O—S— or —S—O—, A is alkyl having 1–6 C atoms, B is O or both H and OH, i.e, together with the

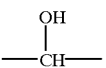

carbon atom to which B is bonded, Hal is F, Cl, Br or I and n is 0, 1 or 2 and their salts.

The compounds are said to be useful for the treatment of cerebrovascular diseases, epilepsy, schizophrenia, Alzheimer's, Parkinson's, or Huntington's disease, cerebral ischaemias or infarctions. However, subtype selectivity is not indicated and, again, piperidine analogs having sulfoxide functionality are not suggested or described.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immuno-deficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

Expression cloning of the first NMDA receptor subunit, NMDAR1 (NR1) in Nakanishi's lab in 1991 provided an initial view of the molecular structure of the NMDA receptor [Nature 354, 31–37 (1991)]. There are several other structurally related subunits (NMDAR2A through NMDAR2D) that join NR1 in heteromeric assemblies to form the functional ion channel complex of the receptor [Annu. Rev. Neurosci. 17, 31–108 (1994)]. The molecular heterogeneity of NMDA receptors implies a future potential for agents with subtype selective pharmacology.

Many of the properties of native NMDA receptors are seen in recombinant homomeric NR1 receptors expressed in Xenopus oocytes. These properties are altered by the NR2 subunits. Recombinant NMDA receptors expressed in Xenopus oocytes have been studied by voltage-clamp recording, as has developmental and regional expression of the mRNAs encoding NMDA receptor subunits. Electrophysiological assays were utilized to characterize the actions of compounds at NMDA receptors expressed in Xenopus oocytes. The compounds were assayed at four subunit combinations of cloned rat NMDA receptors, corresponding to three putative NMDA receptor subtypes [Moriyoshi, et al. Nature 1991, 354, 31–37; Monyer et al, Science 1992, 256, 1217–1221; Kutsuwada et al, Nature 1992, 358, 36–41; Sugihara et al, Biochem. Biophys Res. Commun. 1992, 185, 826–832].

Novel 4-benzyl piperidines that have enhanced subtype selectivity would be highly desirable, particularly for the treatment of Parkinson's disease.

SUMMARY OF THE INVENTION

The invention relates to novel 4-benzyl piperidine alkyl-sulfoxide heterocycles represented by the formula

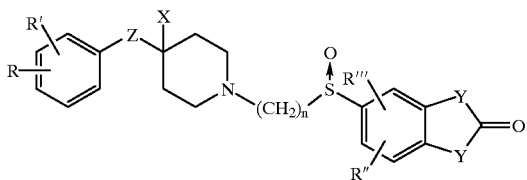

or a stereoisomer or a pharmaceutically acceptable salt thereof, wherein R and R' are independently selected from the group consisting of hydrogen, hydroxy, alkyl, halogen, nitro, cyano, carboxaldehyde, aldehyde amine, lower alkoxy carbonylmethyl, hydroxy lower alkyl, amino carbonylmethyl, hydrazinocarbonylmethyl, acetamido, aryl, aralkyl, amino, a halogenated alkyl group, a lower alkyl amino group or a lower alkoxy group;

R" and R"' are independently selected from the group consisting of hydrogen, hydroxy, alkyl, halogen, amino, a halogenated alkyl group, a lower alkyl amino group or a lower alkoxy group;

X is hydrogen or hydroxy;

Z is —CH$_2$— or

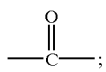

n is 2 to 4; and

Y is O, NH or S.

The compounds of this invention include stereoisomers such as enantiomers as well as the racemic mixtures thereof. A particularly preferred enantiomer of the present invention is (+)-6-{2-[4-(4-fluorobenzyl)piperidin-1-yl]ethanesulfinyl}-3H-benzooxazol-2-one.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate.

Halogen is fluorine, chlorine, bromine, or iodine; fluorine, chlorine, and bromine are preferred groups.

Alkyl means a straight or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Aryl means a monocyclic or bicyclic carbocyclic aromatic ring system which can be substituted or unsubstituted, for example, but not limited to phenyl, naphthyl or the like.

Aralkyl means any of the alkyl groups defined herein substituted by any of the aryl groups as defined herein.

Halogenated alkyl means any of the alkyl groups defined herein substituted by one or more halogens as defined herein.

Lower alkyl amino means any of the alkyl groups defined herein substituted by an amino group.

Lower alkoxy means an alkoxy group containing an alkyl group as defined herein.

The instant invention is also related to a pharmaceutical composition containing the compound of this invention in an amount effective to treat chronic neurodegenerative disorders or cerebrovascular disorders responsive to the selective blockade of NMDA receptor subtypes and a pharmaceutically acceptable carrier. Exemplary disorders responsive to such treatment include cerebral ischemia caused by cerebral trauma, stroke, hypoglycemia, heart attack, and surgery; anxiety-psychosis, schizophrenia; glaucoma; CMV retinitis; antibiotics-induced hearing loss; asthma; urinary incontinence; opioid tolerance or withdrawal; and chronic neurodegenerative disorders such as Huntington's disease, ALS, Parkinson's Disease and Alzheimer's disease. The pharmaceutical composition of this invention may also be employed as an analgesic or for the treatment of convulsions, e.g., epilepsy, or migraine headaches. The pharmaceutical composition of this invention may be used for treating otological diseases including, for example, tinnitus, aminoglycoside antibiotics induced hearing loss and sound induced hearing loss. Ocular diseases such as, for example, glaucoma, CMV retinitis, age related macular degeneration (AMD) and other retinal degenerative diseases may also be treated with the pharmaceutical composition of this invention.

A particularly preferred composition of this invention includes the compound of this invention in combination with dopamine agonists or precursors, e.g., L-DOPA and a pharmaceutically acceptable carrier. The 4-benzyl piperidine alkylsulfoxide heterocycle and L-DOPA are present in an amount effective to treat Parkinson's disease. The composition of this invention may also include other agents used to treat Parkinson's disease, such as for example, pergolide, bromocryptine, pramipexole (mirapas), depreryl, apomorphine and the like.

The invention further relates to a method for treating disorders responsive to the selective blockade of N-methyl-D-aspartate receptor subtypes in an animal suffering thereof which comprises administering in unit dosage form at least one compound of the invention. A particularly preferred embodiment includes the method of treating Parkinson's disease with both a 4-benzyl piperidine alkyl sulfoxide heterocycle and L-DOPA.

DETAILED DESCRIPTION OF THE INVENTION

The novel 4-benzyl piperidine alkylsulfoxide heterocycles of this invention are represented by formula (I). Preferably Z is —CH$_2$—, R" is hydrogen and R"' is hydrogen. More preferably X is hydrogen and R is selected from the group consisting of hydrogen, fluorine, chlorine, bromine and alkyl. More preferably n is 2 and Y is 0. The compounds of this invention are NMDA subtype selective and more particularly NR1A/2B selective.

Exemplary compounds of this invention include 6{2-[4-(4-chloro-benzyl)-piperidin-1-yl]-ethanesulfinyl}-3H-benzooxazol-2-one; 6-{2-[4-(4-fluoro-benzyl)-piperidin-1-yl]-ethanesulfinyl}-3H-benzooxazol-2-one; 6-{2-[4-(4-methyl-benzyl)-piperidin-1-yl]-ethanesulfinyl}3H-benzooxazol-2-one; 6-[2-(4-benzyl-piperidin-1-yl)-ethanesulfinyl]-3H-benzooxazol-2-one; 6-{2-[4-(4-methoxybenzyl)-piperidin-1-yl]-ethanesulfinyl}-3H-benzooxazol- 2-one; 6-{2-[4-(3,4-dichlorobenzyl)-piperidin-1-yl]-ethanesulfinyl}-3H-benzooxazol-2-one; 6-{2-[4-(2-fluorobenzyl)-piperidin-1-yl]-ethanesulfinyl}-3H-benzooxazol-2-one; 6-[2-(4-benzyl-4-hydroxypiperidin-1-yl)-ethanesulfinyl]-3H-benzooxazol-2-one; 6-{2-[4-(4-fluorobenzyl)-4-hydroxy-piperidin-1-yl]-ethanesulfinyl}-3H-benzooxazol-2-one; 6-[2-(4-benzoylpiperidin-1-yl)-ethanesulfinyl]-3H-benzooxazol-2-one; 6-{2-[4-(2,3-difluorobenzyl)-piperidin-1-yl]-ethanesulfinyl}-3H-benzooxazol-2-one; 6-{2-[4-(2,4-difluorobenzyl)-piperidin-1-yl]-ethanesulfinyl}-3H-benzooxazol-2-one; 6-{2-[4-(4- trifluoromethylbenzyl)-piperidin-1-yl}-3H-benzooxazol-2-one; 6-{2-[4-(2,6-difluorobenzyl)-piperidin-1-yl]-ethanesulfinyl}-3H-benzooxazol-2-one; 6-{2-[4-(2,4-dichlorobenzyl)-piperidin-1-yl]-ethanesulfinyl}-3H-benzooxazol-2-one; N-(4-{1-[2-(2-oxo-2,3-dihydrobenzooxazol-6-sulfinyl) ethyl]piperidin-4-ylmethyl}phenyl) acetamide; 6-[2-(4-benzylpiperidin-1-yl) ethanesulfinyl]-5-chloro-3H-benzooxazol-2-one; 5-Chloro-6-{2-[4-(4-fluorobenzyl) piperidin-1-yl]ethanesulfinyl}-3H-benzooxazol-2-one; (+)-6-{2-[4-(4-fluorobenzyl)piperidin-1-yl]ethanesulfinyl}-3H-benzooxazol-2-one; (−)-6-{2-[4,(4-fluorobenzyl)piperidin-1-yl]ethanesulfinyl}-3H-benzooxazol-2-one and pharmaceutically acceptable salts thereof.

The compounds of the present invention are useful in treating or preventing neuronal loss, neurodegenerative diseases and chronic pain. They are also useful as anticonvulsants, as well as for treating epilepsy and psychosis. The therapeutic and side effect profiles of subtype-selective NMDA receptor subtype antagonists should be markedly different from the more non-subtype selective NMDA receptor inhibitors. The subtype-selective analogs of the present invention are expected to exhibit little or no untoward side effects caused by non-specific binding with other sites, particularly, the PCP and glutamate bindings sites associated with the NMDA receptor. In addition, selectivity for different NMDA receptor subtypes will reduce side effects such as sedation that are common to non-subtype-selective NMDA receptor antagonists. The compounds of the present invention are effective in treating or preventing the adverse consequences of the hyperactivity of the excitatory amino acids, e.g. those which are involved in the NMDA receptor system, by preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease, Parkinson's disease and Down's syndrome. The treatment of Parkinson's disease in combination therapy with L-DOPA is particularly preferred.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The selective NMDA receptor subtype antagonists, and modulators may be tested for in vivo anticonvulsant activity after intraperitoneal or intravenous injection using a number of anticonvulsant tests in mice (audiogenic seizure model in DBA-2 mice, pentylenetetrazol-induced seizures in mice, maximum electroshock seizure test (MES) or NMDA-induced death). The compounds may also be tested in drug discrimination tests in rats trained to discriminate PCP from saline. It is expected that most of the compounds of the present invention will not generalize to PCP at any dose. It is expected that such results will suggest that the selective NMDA receptor subtype antagonists of the present invention do not show the PCP-like behavioral side effects that are common to NMDA channel blockers such as MK-801 and PCP or to competitive NMDA antagonists such as CGS 19755.

The selective NMDA receptor subtype antagonists are also expected to show potent activity in vivo after intraperitoneal or intravenous injection suggesting that these compounds can penetrate the blood/brain barrier.

Elevated levels of glutamate has been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment of glaucoma. Preferably, the invention is directed to the treatment of patients which have primary open-angle glaucoma, chronic closed-angle glaucoma, pseudo doexfoliation, or other types of glaucoma or ocular hypertension. Preferably, the compound is administered over an extended period (e.g. at least six months and preferably at least one year), regardless of the changes in the patient's intraocular pressure over the period of administration. The compounds of the present invention are also useful in treating CMV retinitis, particularly in combination with antiviral agents. CMV afflicts the ganglion cell layer which may result in higher levels of glutamate. Thus, NMDA receptor antagonists could block retinitis by blocking the toxicity effect of high levels of glutamate. The compounds of this invention may also find utility in treating other ocular diseases such as AMD and other retinal degenerative diseases.

Aminoglycoside antibiotics have been used successfully in the treatment of serious Gram-negative bacterial infections. However, prolonged treatment with these antibiotics will result in the destruction of sensory hearing cells of the inner ear and consequently, induce permanent loss of hearing. A recent study of Basile, et al. (Nature Medicine, 2:1338–1344, 1996) indicated that aminoglycosides produce a polyamine-like enhancement of glutamate excitotoxicity through their interaction with the NMDA receptor. Thus, compounds of the present invention with NMDA receptor antagonist activity will be useful in preventing aminoglycoside antibiotics-induced hearing loss by antagonizing their interaction with the receptor. The compounds of this invention may also find utility in treating other otological diseases such as tinnitus and sound-induced hearing loss.

The compounds of the present invention are useful in treating headaches, in particular, migraine headaches. During migraine attack, a sensory disturbance with unique changes of brain blood flow will result in the development of characteristic migraine auras. Since this unique phenomena has been replicated in animal experiments with cortical-spreading depression (CSD) of Leaó,A.A.P.J., Neurophysiol. 7:359–390 (1944), CSD is considered an important phenomena in the pathophysiology of migraine with aura (Tepley et al., In: Biomagnetism, eds. S. Williamson, L. Kaufmann, pp. 327–330, Plenum Press, New York (1990)). The CSD is associated with the propagation (2~6 mm/s) of transient changes in electrical activity which relate to the failure of ion homeostatis in the brain, efflux of excitatory amino acids from the neurons and increased energy metabolism (Lauritzen, M., Acta Neurol. Scand. 76 (Suppl. 113): 4–40 (1987)). It has been demonstrated that the initiation of CSD in a variety of animals, including humans, involved the release of glutamate and could be triggered by NMDA (Curtis et al., Nature 191:1010–1011 (1961); and Lauritzen et al., Brain Res. 475:317–327 (1988)). Subtype selective NMDA antagonists will be therapeutically useful for migraine headache because of their expected low side effects, their ability to cross the blood brain barrier and their systemic bioavailability.

Bladder activity is controlled by parasympathetic preganglionic neurons in the sacral spinal cord (DeGroat et al., J. Auton. Nerv. Sys. 3:135–160(1981)). In humans, it has been shown that the highest density of NMDA receptors in the spinal cord are located at the sacral level, including those areas that putatively contain bladder parasympathetic preganglionic neurons (Shaw et al., Brain Research 539:164–168 (1991)). Because NMDA receptors are excitatory in nature, pharmacological blockade of these receptors would suppress bladder activity. It has been shown that the noncompetitive NMDA receptor antagonist MK801 increased the frequency of micturition in rat (Vera and Nadelhaft, Neuroscience Letters 134:135–138(1991)). In addition, competitive NMDA receptor antagonists have also been shown to produce a dose-dependent inhibition of bladder and of urethral sphincter activity (U.S. Pat. No. 5,192,751). Thus, it is anticipated that subtype-selective NMDA receptor antagonists will be effective in the treatment of urinary incontinence mediated by their modulation on the receptor channel activity.

Non-competitive NMDA receptor antagonist MK801 has been shown to be effective in a variety of animal models of anxiety which are highly predictive of human anxiety (Clineschmidt, B. V. et al., Drug Dev. Res. 2:147–163 (1982)). In addition, NMDA receptor glycine site antagonists are shown to be effective in the rat potentiated startle test (Anthony, E. W., Eur. J. Pharmacol. 250:317–324 (1993)) as well as several other animal anxiolytic models (Winslow, J. et al, Eur. J. Pharmacol. 190:11–22 (1990); Dunn, R. et al., Eur. J. Pharmacol. 214:207–214 (1992); and Kehne, J. H. et al, Eur. J. Pharmacol. 193:283–292 (1981)). Glycine site antagonists, (+) HA-966 and 5,7-dichlorokynurenic acid were found to selectively antagonize d-amphetamine-induced stimulation when injected into rat nucleus accumbens but not in striatum (Hutson, P. H. et al., Br. J. Pharmacol. 103:2037–2044 (1991). Interestingly, (+) HA-966 was also found to block PCP and MK801-induced behavioral arousal (Bristow, L. J. et al., Br. J. Pharmacol, 108:1156–1163 (1993)). These findings suggest that a potential use of NMDA receptor channel modulators, but not channel blockers, as atypical neuroleptics.

It has been shown that in an animal model of Parkinson's disease—$MPP^+$ or methamphetamine-induced damage to dopaminergic neurons - can be inhibited by NMDA receptor antagonists (Rojas et al., Drug Dev. Res. 29:222–226 (1993); and Sonsalla et al, Science 243;398–400 (1989)). In addition, NMDA receptor antagonists have been shown to inhibit haloperidol-induced catalepsy (Schmidt, W. J. et al., Amino Acids 1:225–237 (1991)), increase activity in rodents depleted of monoamines (Carlsson et al., Trends Neurosci. 13:272–276 (1990)) and increase ipsilateral rotation after unilateral substantia nigra lesion in rats (Snell, L. D. et al., J. Pharmacol. Exp. Ther. 235:50–57 (1985)). These are also experimental animal models of Parkinson's disease. In animal studies, the antiparkinsonian agent amantadine and memantine showed antiparkinsonian-like activity in animals at plasma levels leading to NMDA receptor antagonism (Danysz, W. et al., J. Neural Trans. 7:155–166, (1994)). Thus, it is possible that these antiparkinsonian agents act therapeutically through antagonism of an NMDA receptor. Therefore, the balance of NMDA receptor activity maybe important for the regulation of extrapyramidal function relating to the appearance of parkinsonian symptoms.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., Science 162:1011–1012 (1968); Way et al., J. Pharmacol. Exp Ther. 167:1–8 (1969); Huidobro et al., J. Pharmacol. Exp Ther. 198:318–329 (1976); Lutfy et al., J. Pharmacol. Exp Ther. 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993); Herman et al., Neuropsychopharmacology 12:269–294 (1995).) Further, it has been reported that NMDA receptor antagonists are useful for inhibiting opioid tolerance and some of the symptoms of opioid withdrawal. Thus, the present invention is also directed to the administration of the compounds described herein to inhibit opiate tolerance and to treat or ameliorate the symptoms of opiate withdrawal by blocking the glycine co-agonist site associated with the NMDA receptor.

It has been suggested that peripheral NMDA receptor activation may be an important mechanism of the airway inflammation and hyper-reactivity exhibited in bronchial asthma. Said, S.J., Trends in Pharmacol. Sci., 20:132–34 (1999). It is reported that this may explain the observations that acute asthmatic attacks may be triggered by food containing glutamate and the ability of ketamine to relax the smooth muscle of the airway, possibly due to the NMDA receptor blocking activity of ketamine. Thus, the compounds of this invention may also be useful in the treatment of asthma.

Thus, the present invention is directed to compounds having high affinity to a particular NMDA receptor subtype and low affinity to other sites such as dopamine and other catecholamine receptors. According to the present invention, those compounds having high binding to a particular NMDA subunit exhibit an $IC_{50}$ of about 100 μM or less in an NMDA subunit binding assay. Preferably, the compounds of the present invention exhibit a selective subunit $IC_{50}$ of 10 μM or less. Most preferably, the compounds of the present invention exhibit a selective subunit $IC_{50}$ of about 1.0 μM or less.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder and post traumatic stress disorders. Preferably, about 0.01 to about 10 mg/kg is orally administered to treat or prevent such disorders or for schizophrenia or other psychoses. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, to treat or prevent glaucoma or urinary incontinence, as well as for the treatment of Alzheimer's disease, amyotrophic lateral sclerosis, Huntington's disease, Parkinson's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, either as an acute intravenous injection, intravenous infusion, or on a regimen of 1–4 times per day. When used to treat chronic pain or migraine headache, to treat or prevent asthma, to induce anesthesia, to treat or prevent convulsions, such as those resulting from epilepsy, to treat depression, to treat or prevent opiate tolerance or to treat opiate withdrawal, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular selective NMDA receptor subtype antagonist of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of NMDA subunit binding sites in vitro has been difficult because of the lack of selective drug ligands. Thus, the compounds of the present invention may be used to characterize the NMDA subunits and their distribution. Particularly preferred subtype-selective NMDA receptor antagonists of the present invention which may be used for this purpose are isotopically radiolabelled derivatives, e.g., where one or more of the atoms are replaced with $^3$H, $^{11}$C, $^{14}$C, $^{15}$N, or $^{18}$F.

The examples which follow are intended as an illustration of certain preferred embodiments of the invention, and no limitation of the invention is implied.

EXAMPLE 1

6-[2-[4-(4-Fluoro-benzyl)-piperidin-1-yl]-ethanesulfinyl]-3H-benzooxazol-2-one

Step A: Preparation of 4-(4-fluorobenzyl)-1-piperidinethanethiol

A mixture of 4-(4-fluorobenzyl)piperidine (5.9 g, 30.5 mmol) and ethyl 2-mercaptoethyl carbonate (4.8 g, 32 mmol) was heated to reflux in toluene (250 mL) for 18 hr under a nitrogen atmosphere. The toluene was removed in vacuo and the resulting oil was used without purification in the next step.

Step B: Preparation of 5-[2-[4-(4-fluorobenzyl)piperidin-1-yl]ethanesulfanyl]-2-nitroanisole A mixture of 4-(4-fluorobenzyl)-1-piperidineethanethiol (7.7 g, 30.4 mmol), 5-bromo-2-nitroanisole (7 g, 30.4 mmol) and $K_2CO$, (4.8 g, 35 mmol) in acetonitrile (250 mL) was heated to reflux for 18 hr under nitrogen. After the mixture had cooled, the salts were removed by filtration and the filtrate concentrated to an oil. The compound was purified by chromatography to provide 6 g of an oil.

Step C: Preparation of 5-[2-[4-(4-fluorobenzyl)piperidin-1-yl]ethanesulfanyl]-2-nitrophenol 5-[2-[4-(4-Fluorobenzyl)piperidin-1-yl]ethanesulfanyl]-2-nitroanisole (6 g) was heated to reflux for 2.5 hr in 48% hydrobromic acid (100 mL), the HBr was distilled off and the residue was partitioned between 2N $Na_2CO_3$ and chloroform (200 mL of each). The organic layer was dried ($MgSO_4$) and concentrated to a solid. Trituration in ethyl ether provided 4.3 g of 5-[2-[4-(4-fluorobenzyl)piperidin-1-yl]ethanesulfanyl]-2-nitrophenol, mp 130–133° C.

Step D: Preparation of 6-{2-[4-(4-fluoro-benzyl)-piperidin-1-yl]-ethanesulfanyl}-3H-benzooxazol-2-one 5-[2-[4-(4-Fluorobenzyl)piperidin-1-yl]ethanesulfanyl]-2-nitrophenol (0.62 g, 1.59 mmol) was dissolved in a 50:50 mixture of tetrahydrofuran and methanol (100 mL). After Raney nickel (0.5 g) was added, the reaction mixture was hydrogenated (50 psi) for 2 hr. The catalyst was removed by filtration and the solvents distilled off to provide the amino phenol that was used immediately. The amino phenol (1.59 mmol) was treated with 1,1'-carbonyldiimidazole (0.5 g, 3 mmol) in tetrahydrofuran (100 mL) and stirred at ambient temperature for 18 hr. Removal of the solvent and purification of the residue by chromatography on silica gel eluting with 5% 1N methanolic ammonia in chloroform gave crude product. Trituration in ethyl ether provided 0.42 g of 6-{2-[4-(4-fluoro-benzyl)-piperidin-1-yl]-ethanesulfanyl}-3H-benzooxazol-2-one, mp 177–179° C.

Step E: Preparation of 6-{2-[4-(4-fluoro-benzyl)-piperidin-1-yl]-ethanesulfinyl}-3H-benzooxazol-2-one A solution of 6-{2-[4-(4-fluoro-benzyl)-piperidin-1-yl]-ethanesulfanyl}-3H-benzooxazol-2-one (1.80 g, 4.55 mmol) in glacial acetic acid (120 mL) was treated with 30% hydrogen peroxide (1 mL, 9 mmol) and stirred at ambient temperature for 18 hr. After ensuring that no peroxide remained, the reaction mixture was concentrated in vacuo and the residue neutralized with aqueous ammonia. The resulting solid was collected by filtration, dried and chromatographed on silica gel eluting with 20% 2N methanolic ammonia in chloroform. The homogenous fractions were combined, concentrated to a solid and triturated in ethyl ether to provide 1.25 g of 6-{2-[4-(4-fluoro-benzyl)-piperidin-1-yl]-ethanesulfinyl}-3H-benzooxazol-2-one, mp 202–204° C.

EXAMPLE 2

6-{2-[4-(4-chloro-benzyl)-piperidin-1-yl]-ethanesulfinyl}-3H-benzooxazol-2-one

The title compound was prepared using a process analogous to Example 1, with the exception that 4-(4-chlorobenzyl)piperidine was employed as a starting material. (mp 213–214° C.)

EXAMPLE 3

6-{2-[4-(4-methyl-benzyl)-piperidin-1-yl]-ethanesulfinyl}-3H-benzooxazol-2-one

The title compound was prepared using a process analogous to Example 1, with the exception that 4-(4-methylbenzyl) piperidine was employed as a starting material. (mp 177–179° C.)

EXAMPLE 4
6-[2-(4-Benzyl-piperidin-1-yl)-ethanesulfinyl]-3H-benzooxazol-2-one The title compound was prepared using a process analogous to Example 1, with the exception that 4-benzyl piperidine was employed as a starting material. (mp 176–178° C.)

EXAMPLE 5
6-{2-[4-(4-methoxybenzyl)-piperidin-1-yl]-ethanesulfinyl}-3H-benzooxazol-2-one The title compound was prepared using a process analogous to Example 1, with the exception that 4-(4-methoxybenzyl)-piperidine was employed as a starting material. (mp 169–170° C.)

EXAMPLE 6
6-{2-[4-(3,4-dichlorobenzyl)-piperidin-1-yl]-ethanesulfinyl}-3H-benzooxazol-2-one The title compound was prepared using a process analogous to Example 1, with the exception that 4-(3,4-dichlorobenzyl)-piperidine was employed as a starting material. (mp 189–191° C.)

EXAMPLE 7
6-{2-[4-(2-fluorobenzyl)-piperidin-1-yl]-ethanesulfinyl}-3H-benzooxazol-2-one The title compound was prepared using a process analogous to Example 1, with the exception that 4-(2-fluorobenzyl)-piperidine was employed as a starting material. (mp 179–181° C.)

EXAMPLE 8
6-[2-(4-benzyl-4-hydroxypiperidin-1-yl)-ethanesulfinyl]-3H-benzooxazol-2-one The title compound was prepared using a process analogous to Example 1, with the exception that 4-benzyl-4-hydroxy-piperidine was employed as a starting material. (mp 138–140° C.)

EXAMPLE 9
6-{2-[4-(4-fluorobenzyl)-4-hydroxy-piperidin-1-yl]-ethanesulfinyl}-3H-benzooxazol-2-one The title compound was prepared using a process analogous to Example 1, with the exception that 4-(4-fluorobenzyl)-4-hydroxy-piperidine was employed as a starting material. (mp 153–155° C.)

EXAMPLE 10
6-[2-(4-benzoylpiperidin-1-yl)-ethanesulfinyl]-3H-benzooxazol-2-one The title compound was prepared using a process analogous to Example 1, with the exception that 4-benzoyl-piperidine was employed as a starting material. (mp 68–72° C.)

EXAMPLE 11
6-{2-[4-(2,3-difluorobenzyl)-piperidin-1-yl]-ethanesulfinyl}-3H-benzooxazol-2-one The title compound was prepared using a process analogous to Example 1, with the exception that 4-(2,3-difluorobenzyl)-piperidine was employed as a starting material. (mp 188–190° C.)

EXAMPLE 12
6-{2-[4-(2,4-difluorobenzyl)-piperidin-1-yl]-ethanesulfinyl}-3H-benzooxazol-2-one The title compound was prepared using a process analogous to Example 1, with the exception that 4-(2,4-difluorobenzyl)-piperidine was employed as a starting material. (mp 166–168° C.)

EXAMPLE 13
6-{2-[4-(4-trifluoromethylbenzyl)-piperidin-1-yl}-3H-benzooxazol-2-one The title compound was prepared using a process analogous to Example 1, with the exception that 4-(4-trifluoromethylbenzyl)-piperidine was employed as a starting material. (mp 165–166° C.)

EXAMPLE 14
6-{2-4[-(2,6-difluorobenzyl)-piperidin-1-yl]-ethanesulfinyl}-3H-benzooxazol-2-one The title compound was prepared using a process analogous to Example 1, with the exception that 4-(2,6-difluorobenzyl)-piperidine was employed as a starting material. (mp 187–189° C.)

EXAMPLE 15
6-{2-[4-(2,4-dichlorobenzyl)-piperidin-1-yl]-ethanesulfinyl}-3H-benzooxazol-2-one The title compound was prepared using a process analogous to Example 1, with the exception that 4-(2,4-dichlorobenzyl)-piperidine was employed as a starting material. (m p 146–148° C.)

EXAMPLE 16
N-(4-{1-[2-(2-oxo-2,3-dihydrobenzooxazol-6-sulfinyl)ethyl]piperidin-4-ylmethyl}phenyl)acetamide The title compound was prepared by using a process analogous to Example 1, with the exception that N-({piperidin-4-ylmethyl}-phenyl)-acetamide was employed as the starting material. (mp 104–105° C.)

EXAMPLE 17
6-[2-(4-benzylpiperidin-1-yl)ethanesulfinyl]-5-chloro-3H-benzooxazol-2-one Step A: Preparation of 5-chloro-6-chlorosulfonyl-3H-benzooxazol-2-one 5-Chloro-3H-benzooxazol-2-one (10.0 g, 59 mmol) was added in portions to chlorosulfonic acid (30 mL) at −20° C. with stirring. The mixture was stirred at room temperature for 2.5 hours and at 70° C. for 1.5 hours. The cooled reaction mixture was poured slowly into iced-water (300 mL) and stirred for 1 hour. The precipitate was collected and washed with water. The dried precipitate was stirred in chloroform (500 mL) for 3 hours at room temperature, filtered off and dried to give 12.3 g of a pale pink solid.

Step B: Preparation of 5-chloro-6-sulfanyl-3H-benzooxazol-2-one

Zinc dust (14.4 g, 0.22 mol) was added to a solution of mercuric chloride (2.86 g, 10.6 mmol) in water (42 mL) and concentrated hydrochloric acid (1.7 mL). The mixture was stirred for 15 min and the supernatant poured off. The residue was washed with water (2×15 mL), ethanol (2×15 mL) and diethyl ether (2×15 mL). 5-chloro-6-chlorosulfonyl-3H-benzooxazol-2-one (12.3 g, 46 mmol) and ethanol (70 mL) were added to the residue and the mixture placed in an ice-bath. Concentrated hydrochloric acid (36 mL) was added via addition funnel over 15 min and the resulting mixture stirred at reflux for 18 hours. The cooled reaction mixture was poured into ice-cold water (300 mL) and stirred for 20 min. The precipitate was collected to give 9.5 g of a white powder.

Step C: Preparation of 5-chloro-{6-chloroethanesulfanyl}-3H-benzooxazol-2-one 1,8-Diazabicyclo[5.4.0]undec-7-ene (7.2 mL, 48 mmol) was added to 5-chloro-6-sulfanyl-3H-benzooxazol-2-one (9.5 g, 47 mmol) and 1-bromo-2-chloroethane (17.3 mL, 0.21 mol) in acetonitrile (80 mL) at 0° C. with stirring. The resulting solution was stirred at room temperature overnight. The reaction mixture was poured into ice-cold water (200 mL) and the precipitate collected. The precipitate was dissolved in ethyl acetate (350 mL), dried over magnesium sulfate, filtered and evaporated to leave 6.0 g of an off-white solid.

Step D: Preparation of 5-chloro-{6-chloroethanesulfinyl}-3H-benzooxazol-2-one

Sodium periodate (2.49 g, 11.7 mmol) was added to 5-chloro-{6-chloroethanesulfanyl}-3H-benzooxazol-2-one (3.08 g, 11.7 mmol) in methanol (300 mL) and water (80 mL) at 0° C. with stirring. The resulting mixture was stirred at room temperature for 1 hour then more sodium periodate (2.49 g, 11.7 mmol) was added at 0° C. and the mixture stirred at room temperature for 3 days. Water (500 mL) was added and the mixture extracted with chloroform (3×300 mL). The extracts were dried over magnesium sulfate, filtered and evaporated to give 3.1 g of a brown solid.

Step D: Preparation of 6-[2-(4-benzylpiperidin-1-yl)ethanesulfinyl]-5-chloro-3H-benzooxazol-2-one 4-benzylpiperidine (0.2 mL, 1.2 mmol) in acetonitrile (5 mL) was treated with 5-chloro-{6-chloroethanesulfinyl}-3H-benzooxazol-2-one (300 mg, 1.1 mmol), 2N NaOH (0.5 mL) and water (0.5 mL). The mixture was stirred at 60° C. under argon for 30 min. More 2N NaOH (0.5 mL) was added and the mixture stirred a further 2 hours at 60° C. The mixture was cooled to room temperature and the pH adjusted to 6. The precipitate was filtered off and dried to give 0.26 g of a powder. The powder was recrystallized from hot EtOAc (30 mL) and methanol (20 mL) to give 0.14 g of 6-[2-(4-benzylpiperidin-1-yl)ethanesulfinyl]-5-chloro-3H-benzooxazol-2-one, a white powder. (mp 190–192° C.)

EXAMPLE 18
5-Chloro-6-{2-[4-(4-fluorobenzyl)piperidin-1-yl]ethanesulfinyl}-3H-benzooxazol-2-one The title compound was prepared using a process analogous to Example 17, with the exception that 4-(4-fluorobenzyl)piperidine was employed as a starting material. (mp 199–200° C.)

EXAMPLE 19
(+)-6-{2-[4-(4-fluorobenzyl)piperidine-1-yl]ethanesulfinyl}-3H-benzooxazol-2-one 6-chloroethanesulfinyl-3H-benzooxazol-2-one was prepared using a process analogous to Example 17, steps A–D, with the exception that 3H-benzooxazol-2-one was employed as a starting material.

The enantiomers of 6-chloroethanesulfinyl-3H-benzooxazol-2-one were separated by liquid chromatography on a 20×250 mm chirobiotic-T column eluting with ethanol at 2 mL/min. The faster-eluting enantiomer was coupled with 4-(4-fluorobenzyl)piperidine using a process analogous to Example 17, step E to give the title compound. (mp 150–155° C.)

$[\alpha]_{20}^D = +124°$ (C=0.002, 1% CF$_3$CO$_2$H in MeOH).

EXAMPLE 20
(−)-6-{2-[4,(4-fluorobenzyl)piperidin-1-yl]ethanesulfinyl}-3H-benzooxazol-2-one The title compound was prepared using a process analogous to Example 19, with the exception that the slower-eluting enantiomer was obtained. (mp 150–155° C.)

$[\alpha]_{20}^D = -146°$ (C=0.002, 1% CF$_3$CO$_2$H in MeOH).

The compounds of this invention prepared above were tested by electrophysiological assays at NMDA receptor subunits and were found to be subtype-selective NMDA antagonists.

Electrophysiological Assays at NMDA receptor subunits.
Preparation of RNA.

cDNA clones encoding the NR1A, NR2A, NR2B, and NR2C rat NMDA receptor subtypes were used. (See, Moriyoshi et al., *Nature* (lond.) 354:31–37 (1991); Kutsuwada et al., *Nature* (Lond.) 358:36–41 (1992) Monyer et al., *Science* (Washington, D.C.) 256:1217–1221 (1992); Ikeda et al., *FEBS Lett.* 313:34–38 (1992); Ishii et al., *J. Biol. Chem.* 268:2836–2843(1993) for details of these clones or their mouse homologs). The clones were transformed into appropriate host bacteria and plasmid preparations were made with conventional DNA purification techniques. A sample of each clone was linearized by restriction enzyme digestion and cRNA was synthesized with T3 RNA polymerase. The cRNA was diluted to 400 ng/μl and stored in 1 μl aliquots at −80° C. until injection.

The Xenopus Oocyte Expression System

Mature female *Xenopus laevis* were anaesthetized (20–40 min) using, 0.15% 3-aminobenzoic acid ethyl ester (MS-222) and 2–4 ovarian lobes were surgically removed. Oocytes at developmental stages IV—VI (Dumont, J. N., *J. Morphol.* 136:153–180 (1972)), were dissected from the ovary still surrounded by enveloping ovarian tissues. Follicle-enclosed oocytes were micro-injected with 1:1 mixtures of NR1A:NR2A, 2B or 2C; infecting 1–10 ng of RNA encoding each receptor subunit. NR1A encoding RNA was injected alone at ~20 ng. Oocytes were stored in Barth's medium containing (in mM):NaCl, 88; KCl, 1; CaCl$_2$, 0.41; Ca(NO$_3$)$_2$, 0.33; MgSo$_4$, 0.82 NaHCO$_3$, 2.4; HEPES 5, pH 7.4, with 0.11 mg/ml gentamicin sulphate. While oocytes were still surrounded by enveloping ovarian tissues the Barth's medium was supplemented with 0.1% bovine serum. Oocytes were defolliculated 1–2 days following injections by treatment withcollagenase (0.5 mg/ml Sigma Type I for 0.5–1 hr) (Miledi and Woodward, *J. Physiol.* (Lond.) 416:601–621 (1989)) and subsequently stored in serum-free medium.

Electrical recordings were made using a conventional two-electrode voltage clamp (Dagan TEV-200) over periods ranging between 3–21 days following injection. (Woodward et al., *Mol. Pharmacol.* 41: 89–103 (1992)). Oocytes were placed in a 0.1 ml recording chamber continuously perfused (5–15 ml min$^{-1}$) with frog Ringer's solution containing (in mM):NaCl, 115; KCL, 2; BaCl$_2$, 1.8; HEPES, 5; pH 7.4. Drugs were applied by bath perfusion. Using oocytes expressing different subunit combinations of NMDA receptor, NMDA currents were activated by co-application of glutamate (100 μM) and glycine (1–100 μM). Inhibitory potency of the novel antagonists was assessed on responses elicited by fixed concentrations of glutamate and glycine, by measuring reductions in current induced by progressively increasing concentrations of antagonist. Concentration-inhibition curves were fit with equation 1.

$$I/I_{control} = 1/(1+([\text{antagonist}]/10^{-pIC_{50}})^n) \quad \text{Eq. 1}$$

in which $I_{control}$ is the current evoked by agonists alone, $pIC_{50} = -\log IC_{50}$, $IC_{50}$ is the concentration of antagonist that produces half maximal inhibition, and n is the slope factor. (De Lean et al., *Am. J. Physiol.* 235: E97–102 (1978)). For incomplete curves analysis by fitting was unreliable and $IC_{50}$ values were calculated by simple regression over linear portions of the curves (Origin: Microcal Software).

The electrophysiological assay results are set forth in Table 1.

6-OHDA Rat Assay

6-Hydroxydopamine-lesioned rats were used (See Ungerstedt, U.; Arbuthnott, G. W., Quantitative recording of rotational behavior in rats after 6-hydroxy-dopamine lesions of the nigrostraiatal dopamine system. *Brain Res.* 1971, 24(3), 485–93). Adult male Sprague-Dawley rats were anesthetized with chloral hydrate and unilateral lesions of the nigrostriatal dopamine system were accomplished by infusion of 8 μg of 6-hydroxydopamine HBr (6-OHDA) into the right medial forebrain bundle. Rats were pretreated 30 minutes before surgery with desipramine HCl 25 mg/kg intraperitoneally (IP) to protect noradrenergic neurons, and pargyline 25 mg/kg IP to potentiate the effects of 6-OHDA. A minimum of 3 weeks after surgery, the rotational behavior induced by apomorphine HCL 50 μg/kg subcutaneously (SC) was assessed. Only rats demonstrating more than 100 contraversive turns/hour to apomorphine were used for the present experiments. Rotational behavior was measured using an automatic rotometer system (Rotorat Rotational Activity System, MED Associates, Georgia, Vt.). Anti-parkinsonian activity was assessed as the ability of the compound to potentiate the contraversive rotation induced by L-DOPA methyl ester, 10 mg/kg SC, over a 6 hour period. Experiments were conducted using a crossover paradigm where each rat received either a vehicle plus L-DOPA, or the test compound plus L-DOPA, in randomized order. Rats were tested at 7 day intervals. In experiments in which the compound was tested orally, rats were food deprived for 16 hours. Statistical analysis between treatment groups were performed using a paired t-test. The results are reported in Table 1 as the minimum effective dose (MED) of compound required to produce a statistically-significant increase in total contraversive rotations compared to rats receiving L-DOPA only.

TABLE 1

| Example | NRI$_A$/2A IC$_{50}$ μM | NR1$_A$/2B IC$_{50}$ μM | NR1$_A$/2C IC$_{50}$ μM | 6-OHDA rat MED mg/kg po |
|---|---|---|---|---|
| 1 | 105 | 0.03 | 190 | 1 |
| 2 | >300 | 0.02 | 200 | 3 |
| 3 | 100 | 0.03 | | 3 |
| 4 | >300 | 0.03 | >300 | 3 |
| 5 | 55 | 0.10 | 150 | >10 |
| 6 | 70 | 0.10 | 80 | >10 |
| 7 | 55 | 0.09 | 60 | 10 |
| 8 | 40 | 1.10 | 230 | — |
| 9 | 50 | 0.90 | 200 | >10 |
| 10 | 70 | 0.34 | 140 | — |
| 11 | 40 | 0.05 | 140 | 10 |
| 12 | 30 | 0.01 | 130 | 10 |
| 13 | 35 | 0.04 | 150 | 10 |
| 14 | 55 | 0.04 | 160 | >10 |
| 15 | 90 | 0.04 | 150 | 10 |
| 16 | >300 | 10 | >300 | — |
| 17 | 40 | 0.16 | >300 | >10 |
| 18 | 35 | 0.11 | >300 | >10 |
| 19 | — | 0.03 | — | 1 |
| 20 | — | 0.03 | — | 30 |

Other variations and modifications of this invention will be obvious to those skilled in this art. This invention is not to be limited except as set forth in the following claims.

What is claimed is:
1. A compound represented by the formula

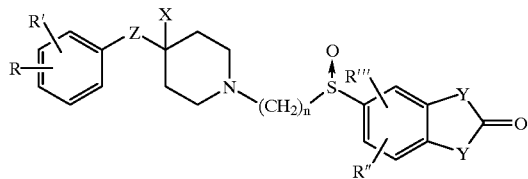

or stereoisomers or a pharmaceutically acceptable salt thereof, wherein R and R' are independently selected from the group consisting of hydrogen, hydroxy, alkyl, halogen, nitro, cyano, carboxaldehyde, aldehyde amine, lower alkoxy carbonylmethyl, hydroxy lower alkyl, amino carbonylmethyl, hydrazinocarbonylmethyl, acetamido, aryl, aralkyl, amino, a halogenated alkyl group, a lower alkyl amino group or a lower alkoxy group;

R" and R'" are independently selected from the group consisting of hydrogen, hydroxy, alkyl, halogen, amino, a halogenated alkyl group, a lower alkyl amino group or a lower alkoxy group;

X is hydrogen or hydroxy;

Z is —CH$_2$— or

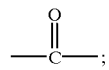

n is 2 to 4; and
Y is O, NH or S.

2. A compound according to claim 1, wherein Z is —CH$_2$—, R" is hydrogen and R'" is hydrogen.
3. A compound according to claim 2, wherein R' is hydrogen and X is hydrogen.
4. A compound according to claim 3, wherein R is selected from the group consisting of hydrogen, fluorine, chlorine, bromine and alkyl.
5. A compound according to claim 4, wherein n is 2.
6. A compound according to claim 5, wherein Y is 0.
7. A compound according to claim 5, wherein said compound is selected from the group consisting of 6-{2-[4-(4-chloro-benzyl)-piperidin-1-yl]-ethanesulfinyl}-3H-benzooxazol-2-one; 6-{2-[4-(4-fluoro-benzyl)-piperidin-1-yl]-ethanesulfinyl}-3H-benzooxazol-2-one; 6-{2-[4-(4-methyl-benzyl)-piperidin-1-yl]-ethanesulfinyl}3H-benzooxazol-2-one; 6-[2-(4-benzylpiperidin-1-yl)-ethanesulfinyl]-3H-benzooxazol-2-one; 6-{2-[4-(4-methoxybenzyl)-piperidin-1-yl]-ethanesulfinyl}-3H-benzooxazol-2-one; 6-{2-[4-(3,4-dichlorobenzyl)-piperidin-1-yl]-ethanesulfinyl}-3H-benzooxazol-2-one; 6-{2-[4-(2-fluorobenzyl)-piperidin-1-yl]-ethanesulfinyl}-3H-benzooxazol-2-one; 6-[2-(4-benzyl-4-hydroxypiperidin-1-yl)-ethanesulfinyl]-3H-benzooxazol-2-one; 6-{2-[4-(4-fluorobenzyl)-4-hydroxypiperidin-1-yl]-ethanesulfinyl}-3H-benzooxazol-2-one; 6-[2-(4-benzoylpiperidin-1-yl)-ethanesulfinyl]-3H-benzooxazol-2-one; 6-{2-[4-(2,3-difluorobenzyl)-piperidin-1-yl]-ethanesulfinyl}-3H-benzooxazol-2-one; 6-{2-[4-(2,4-difluorobenzyl)-piperidin-1-yl]-ethanesulfinyl}-3H-benzooxazol-2-one; 6-{2-[4-(4-trifluoromethylbenzyl)-piperidin-1-yl]-3H-benzooxazol-2-one; 6-{2-[4-(2,6-difluorobenzyl)-piperidin-1-yl]-ethanesulfinyl}-3H-benzooxazol-2-one; 6-{2-[4-(2,4-dichlorobenzyl)-piperidin-1-yl]-ethanesuifinyl}-3H-benzooxazol-2-one; N-(4-{1-(2-(2-oxo-2,3- dihydrobenzooxazol-6-sulfinyl)ethyl]piperidin-4-ylmethyl}phenyl)acetamide; 6-[2-(4-benzylpiperidin-1-yl) ethanesulfinyl]-5-chloro-3H-benzooxazol-2-one; 5-Chloro-6-{2-[4-(4-fluorobenzyl)piperidin-1-yl]ethanesulfinyl}-3H-benzooxazol-2-one; (+)-6-{2-[4-(4-fluorobenzyl)piperidine-1-yl]ethanesulfinyl}-3H-benzooxazol-2-one; (−)-6-{2-[4,(4-fluorobenzyl)piperidin-1-yl]ethanesulfinyl}-3H-benzooxazol-2-one and pharmaceutically acceptable salts thereof.

8. A compound according to claim 1, wherein said compound is 6-[2-[-(4-Fluoro-benzyl)-piperidin-1-yl]-ethanesulfinyl]-3H-benzooxazol-2-one or a pharmaceutically acceptable salt thereof.

9. An enantiomer of 6-[2-[4-(4-Fluoro-benzyl)-piperidin-1-yl]-ethanesulfinyl]-3H-benzoorazol-2-one or a pharmaceutically acceptable salt thereof, wherein said enantiomer is present in at least 50% enantiomeric excess with respect to the other enantiomer.

10. An enantiomer of claim 9, wherein said enantiomer is (+)-6-{2-[4-(4-fluorobenzyl)piperidin-1-yl] ethanesulfinyl}-3H-benzooxazol-2-one.

11. A pharmaceutical composition comprising a pharmaceutically acceptable carrier or diluent and a therapeutically effective amount of at least one compound of claims 1 to 10.

12. A pharmaceutical composition according to claim 11, wherein said composition is useful for treating disorders responsive to the selective blockade of N-methyl-D-aspartate receptor subtypes selected from the group consisting of stroke, cerebral ischemia, central nervous systems, trauma, hypoglycemia, neurodegenerative disorders, anxiety, migraine headache, convulsions, tinnitus, aminoglycoside antibiotics-induced hearing loss, macular or retinal degeneration, psychosis, glaucoma, depression, asthma, CMV retinitis, opioid tolerance or withdrawal, chronic pain, or urinary incontinence.

13. A pharmaceutical composition according to claim 12, wherein said neurodegenerative disorder is Parkinson's disease.

14. A pharmaceutical composition according to claim 13, further comprising a dopamine agonist or precursor thereof in amount effective to treat Parkinson's disease.

15. A pharmaceutical composition according to claim 14, wherein said dopamine agonist is L-DOPA.

16. A pharmaceutical composition comprising (+)-6-{2-4-(4-fluorobenzyl)piperidin-1-yl]ethanesulfinyl}-3H-benzooxazol-2-one or a pharmaceutically acceptable salt thereof, substantially free of (−)-6-{2-[4-(4-fluorobenzyl) piperidin-1-yl]ethanesulfinyl}-3H-benzooxazol-2-one, and a pharmaceutically acceptable carrier or diluent.

17. A pharmaceutical composition according to claim 16, further comprising L-DOPA.

18. A method for treating disorders responsive to the selective blockade of N-methyl-D-aspartate receptor subtypes in an animal suffering thereof which comprises administering in unit dosage form at least one compound represented by the formula

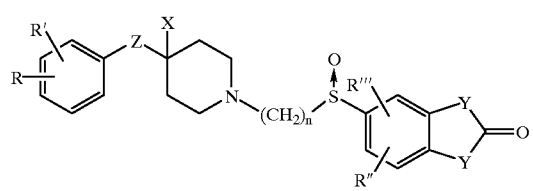

or a stereoisomer or a pharmaceutically acceptable salt thereof, wherein R is selected from the group consisting of hydrogen, hydroxy, alkyl, halogen, nitro, cyano, carboxaldehyde, aldehyde amine, lower alkoxy carbonylmethyl, hydroxy lower alkyl, amino carbonylmethyl, hydrazinocarbonylmethyl, acetamido, aryl, aralkyl, amino, a halogenated alkyl group, a lower alkyl amino group or a lower alkoxy group;

R" and R'" are independently selected from the group consisting of hydrogen, hydroxy, alkyl, halogen, amino, a halogenated alkyl group, a lower alkyl amino group or a lower alkoxy group;

X is hydrogen or hydroxy;

Z is —CH$_2$— or

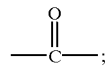

n is 2 to 4; and

Y is O, NH or S.

19. A method according to claim 18, wherein Z is —CH$_2$—, R" is hydrogen and R'" is hydrogen.

20. A method according to claim 18, wherein said disorder is selected from the group consisting of stroke, cerebral ischemia, central nervous system disorders, trauma, hypoglycemia, neurodegenerative disorders, anxiety, migraine headache, convulsions, tinnitus, aminoglycoside antibiotics-induced hearing loss, psychosis, macular or retinal degeneration, glaucoma, CMV retinitis, asthma, opioid tolerance or withdrawal, chronic pain, depression or urinary incontinence.

21. A method according to claim 18, wherein said disorder is Parkinson's disease.

22. A method according to claim 18, wherein said disorder is chronic pain.

23. A method according to claim 18, wherein said disorder is depression.

24. A method according to claim 18, wherein said disorder is convulsions.

25. A method according to claim 21, further comprising administering in unit dosage form a dopamine agonist to said animal suffering from Parkinson's disease.

26. A method according to claim 25, wherein said dopamine agonist is L-DOPA.

27. A method for treating disorders responsive to the selective blockade of N-methyl-D-asparate receptor subtypes in an animal suffering thereof which comprises administering in unit dosage form (+)-6-{2-[4-(4-fluorobenzyl) piperidin-1-yl]ethanesulfinyl}-3H-benzooxazol-2-one or a pharmaceutically acceptable salt thereof, substantially free of (−)-6-{2-[4-(4 -fluorobenzyl)piperidin-1-yl) ethanesultinyl}-3H-benzooxazol-2-one.

28. A method according to claim 27, wherein said method further comprises administering L-DOPA in unit dosage form to said animal.

* * * * *

UNITED STATES PATENT AND TRADEMARK OFFICE
CERTIFICATE OF CORRECTION

PATENT NO.    : 6,284,774 B1
DATED         : September 4, 2001
INVENTOR(S)   : Jonathan L. Wright et al.

It is certified that error appears in the above-identified patent and that said Letters Patent is hereby corrected as shown below:

Title Page,
Item 56, References Cited: OTHER PUBLICATIONS, after "M. Gossel et al.", Dimentia" should read -- Dementia -- and after "Said, S.J.", "pp. 132-134)" should read -- pp. 132-134 -- and "1999." should read -- (1999). --.

Item [73], Assignee, after "NJ (US)" should read -- ; CoCensys, Inc., Irvine, CA (US) --.

Column 3,
Line 3, "formula" should read -- formula (I): --.

Column 6,
Line 36, "pseudo doexfoliation," should read -- pseudo exfoliation, --.

Column 7,
Line 11, "homeostatis" should read -- homeostasis --.

Column 8,
Line 16, "maybe" should read -- may be --.

Column 11,
Line 40, "include," should read -- including, --.

Column 12,
Line 5, "$K_2CO$," should read -- $K_2CO_3$ --.

Column 14,
Line 24, "(m p" should read -- (mp --.

Column 15,
Line 64, "($mp^{150-155º}$ C.) should read -- (mp 150-155º C.) --

Column 16,
Line 9, "(lond.)" should read -- (Lond.) --;
Line 10, "(1992)" should read -- (1992); --;
Line 29, "infecting" should read -- injecting --;
Line 33, "0.82" should read -- 0.82; --; and
Line 38, "withcollagenase" should read -- with collagenase --.

UNITED STATES PATENT AND TRADEMARK OFFICE
CERTIFICATE OF CORRECTION

PATENT NO. : 6,284,774 B1
DATED : September 4, 2001
INVENTOR(S) : Jonathan L. Wright et al.

It is certified that error appears in the above-identified patent and that said Letters Patent is hereby corrected as shown below:

Column 17,
Line 18, "nigrostraiatal" should read -- nigrostriatal --.

Column 18,
Line 43, "claim 5," should read -- claim 1, --; and
Line 48, "-ethanesulfinyl}3H-" should read -- -ethanesulfinyl}-3H --.

Column 19,
Line 6, "1-yllethanesulfinyl}" should read --1-yl]-ethanesulfinyl} --; and
Line 29, "systems," should read -- system disorders --.

Column 20,
Line 20, "R is" should read -- R and R' are independently --.

Signed and Sealed this

Twenty-fifth Day of June, 2002

Attest:

JAMES E. ROGAN
Attesting Officer
Director of the United States Patent and Trademark Office